(12) United States Patent
Zahrt

(10) Patent No.: US 11,406,262 B2
(45) Date of Patent: Aug. 9, 2022

(54) NYSTAGMUS TESTING DEVICE AND METHOD

(71) Applicant: Peter F. Zahrt, Floyd, VA (US)

(72) Inventor: Peter F. Zahrt, Floyd, VA (US)

( * ) Notice: Subject to any disclaimer, the term of this patent is extended or adjusted under 35 U.S.C. 154(b) by 344 days.

(21) Appl. No.: 16/383,739

(22) Filed: Apr. 15, 2019

(65) Prior Publication Data
US 2019/0313897 A1    Oct. 17, 2019

Related U.S. Application Data

(60) Provisional application No. 62/657,374, filed on Apr. 13, 2018.

(51) Int. Cl.
*A61B 3/113* (2006.01)
*A61B 3/14* (2006.01)
*A61B 3/00* (2006.01)

(52) U.S. Cl.
CPC ............ *A61B 3/113* (2013.01); *A61B 3/0041* (2013.01); *A61B 3/14* (2013.01)

(58) Field of Classification Search
CPC ......... A61B 3/00; A61B 3/0041; A61B 3/113; A61B 3/14; A61B 3/005; A61B 3/02; A61B 3/10; A61B 3/103; A61B 3/032; A61B 3/024; A61B 5/00; A61B 5/4863
USPC ....... 351/210, 218, 205, 206, 209, 221, 246; 600/112, 162, 558, 587
See application file for complete search history.

(56) References Cited

U.S. PATENT DOCUMENTS

| | | | |
|---|---|---|---|
| 7,357,507 B2 | 4/2008 | Waldorf et al. | |
| 7,388,166 B2 | 6/2008 | Marmaropoulos et al. | |
| 8,764,194 B2 | 7/2014 | Harris et al. | |
| 8,899,748 B1 * | 12/2014 | Migdal | A61B 5/4863 351/206 |
| 2007/0182929 A1 * | 8/2007 | Feher | A61B 3/113 351/243 |

OTHER PUBLICATIONS

DAX Admissibility Opinion Letter, dated Jul. 6, 2015, 5 pages.
DAX Evidence Recorder brochure, 2017, 2 pages.
Ocular Data Systems DAX Evidence Recorder, available at https://www.youtube.com/watch?v=xV7Ha3VDbzE, dated Dec. 1, 2015.

* cited by examiner

*Primary Examiner* — Jie Lei
(74) *Attorney, Agent, or Firm* — Barnes & Thornburg LLP (57) ABSTRACT

A device, system, and method for operating a nystagmus testing device is disclosed. The device comprising a camera configured to face a test subject to capture eye movements of the test subject, a start button configured to start a nystagmus routine, a front display positioned to face the test subject configured to display a visual stimulus, a rear display positioned to face a test administrator configured to display a visual tracker, and a controller configured to control movements of the visual stimulus and the visual tracker on the front and rear display, respectively, and generate data of the nystagmus routine.

15 Claims, 12 Drawing Sheets

NYSTAGMUS TESTING DEVICE AND METHOD

CROSS-REFERENCE TO RELATED APPLICATION

This application claims the benefit of U.S. Provisional Patent Application No. 62/657,374, filed Apr. 13, 2018, the entire disclosure of which is incorporated by reference herein.

TECHNICAL FIELD

The present disclosure relates generally to a nystagmus test.

BACKGROUND

Field sobriety tests are used to enforce DUI laws. One of the components of field sobriety tests involves horizontal gaze nystagmus (HGN), which is the involuntary jerking of one's eye when it gazes to the side. Since this jerking becomes exaggerated by alcohol consumption, it is used as evidence of impairment in DUI cases. Typically, HGN test is conducted by a test administrator or an officer by a physical observation of a test subject's eye movement. Although the scientific basis for HGN and the general method of applying it are sufficiently reliable to allow admission without proof of these elements in each case, some degree of proof that the test was administered correctly is required to be admissible in court.

SUMMARY

According to one aspect of the disclosure, a method for operating a nystagmus testing device, the method including receiving a start signal to start a nystagmus routine, the nystagmus routine including a plurality of tests, illuminating, in response to receiving the start signal, an indicator indicative of a corresponding test of the nystagmus routine, conducting, in response to receiving the start signal, the corresponding test by (i) moving a visual stimulus on a front display of the nystagmus testing device facing a test subject and (ii) moving a visual tracker on a rear display of the nystagmus testing device facing a test administrator, recording, in response to conducting the corresponding test, data associated with the corresponding test, and advancing to a next test of the nystagmus routine.

In some embodiments, each of the plurality of tests may be directed to determining one of lack of smooth pursuit, distinct and sustained nystagmus at maximum deviation, onset of nystagmus prior to 45 degrees, and vertical gaze nystagmus.

In some embodiments, the indicator may be one of a visual indicator and an audible indicator.

In some embodiments, the visual indicator may illuminate a first color indicating that the corresponding test is ready or completed and a second color indicating that the corresponding test is started.

In some embodiments, the method may further include receiving a restart signal to restart the corresponding test, and conducting, in response to receiving the start signal, the corresponding test by moving the visual stimulus on the front display of the nystagmus testing device and moving the visual tracker on the rear display of the nystagmus testing device.

In some embodiments, the method may further include determining whether the corresponding test is completed.

In some embodiments, determining whether the corresponding test is completed may include determining whether the nystagmus testing device was stable for a predefined period of time.

In some embodiments, determining whether the nystagmus testing device was stable for a predefined period of time may include determining whether a pressure sensor signal received from at least one pressure sensor was within a predetermined range for a predefined period of time.

In some embodiments, determining whether the nystagmus testing device was stable for a predefined period of time may include determining whether the nystagmus testing device was leveled or plumbed for a predefined period of time.

In some embodiments, the method may further include illuminating, in response to receiving the start signal, an LED light, wherein the LED light is configured to illuminate a first color indicating that the corresponding test is ready or completed and a second color indicating that the corresponding test has started.

In some embodiments, the data may include eye movements of the test subject and positions of the visual stimulus during the corresponding test.

In some embodiments, the method may further include displaying the data of the corresponding test, wherein displaying the data comprises displaying eye movements of the test subject relative to the position of the visual stimulus.

In some embodiments, the method may further include receiving a test selection signal indicative of a next test of the nystagmus routine, performing, in response to receiving the test selection signal, the next test by moving the visual stimulus on the front display of the nystagmus testing device and moving the visual tracker on the rear display of the nystagmus testing device, and recording, in response to conducting the next test, data associated with the next test.

In some embodiments, the method may further include positioning the nystagmus testing device in front of the test subject.

In some embodiments, the method may further include monitoring, by the test administrator, an eye movement of the test subject with respect to a position of the visual tracker displayed on the rear display.

In some embodiments, the method may further include receiving a signal indicative of a present sense impression of the test administrator when one or more signs of intoxication were observed during the test.

According to another aspect, a nystagmus testing device includes a camera facing a test subject to capture eye movements of the test subject, a start button configured to start a nystagmus routine, the nystagmus routine including a plurality of tests, a front display facing the test subject configured to display a visual stimulus, a rear display facing a test administrator configured to display a visual tracker, and a controller configured to control movements of the visual stimulus and the visual tracker on the front and rear displays, respectively, and generate data of the nystagmus routine.

In some embodiments, each of the plurality of tests may be directed to determining one of lack of smooth pursuit, distinct and sustained nystagmus at maximum deviation, onset of nystagmus prior to 45 degrees, and vertical gaze nystagmus.

In some embodiments, the nystagmus testing device may further include an indicator indicative of a corresponding test of the nystagmus routine, wherein the indicator is one of a visual indicator and an audible indicator.

In some embodiments, the visual indicator may be configured to illuminate a first color indicating that the corresponding test is ready or completed and a second color indicating that the corresponding test is started.

In some embodiments, the nystagmus testing device may further include a test restart button to restart the corresponding test.

In some embodiments, the nystagmus testing device may further include a test selection button configured to select one test of the nystagmus routine.

In some embodiments, the nystagmus testing device may further include a plurality of pressure sensors configured to determine a stability of the nystagmus testing device.

In some embodiments, the nystagmus testing device may further include a LED light configured to illuminate a first color indicating that the corresponding test is ready or completed and a second color indicating that the corresponding test has started.

In some embodiments, the controller may further include a memory that is configured to store data associated with the corresponding test.

In some embodiments, the data may include eye movements of the test subject and positions of the visual stimulus during the corresponding test.

In some embodiments, the nystagmus testing device may further include an external display to display the data associated with the corresponding test.

In some embodiments, the nystagmus testing device may further include an indicator button configured to be depressed by the test administrator during the test indicating one or more signs of intoxication.

According to another aspect, a nystagmus testing system includes a telescopic pole, and a nystagmus testing device supported on the pole. The nystagmus testing device includes a front display facing a test subject, a rear display facing a test administrator, a camera, a start button configured to start a nystagmus routine, the nystagmus routine includes a plurality of tests, and a controller configured to control the front and rear displays.

In some embodiments, each of the plurality of tests is directed to determining one of lack of smooth pursuit, distinct and sustained nystagmus at maximum deviation, onset of nystagmus prior to 45 degrees, and vertical gaze nystagmus.

In some embodiments, the nystagmus testing device may further include an indicator indicative of a corresponding test of the nystagmus routine.

In some embodiments, the indicator may be one of a visual indicator and an audible indicator.

In some embodiments, the visual indicator may be configured to illuminate a first color indicating that the corresponding test is ready or completed and a second color indicating that the corresponding test is started.

In some embodiments, the nystagmus testing device may further include a test restart button to restart the corresponding test.

In some embodiments, the nystagmus testing device may further include a test selection button configured to select one test of the nystagmus routine.

In some embodiments, the nystagmus testing device may further include a plurality of pressure sensors configured to determine a stability of the nystagmus testing device.

In some embodiments, the nystagmus testing device may further include a LED light configured to illuminate a first color indicating that the corresponding test is ready or completed and a second color indicating that the corresponding test has started.

In some embodiments, the front display may be configured to display a visual stimulus and the rear display may be configured to display a visual tracker. The controller may be configured to control movements of the visual stimulus and the visual tracker and generate data.

In some embodiments, the data may include eye movements of the test subject and positions of the visual stimulus during the corresponding test.

In some embodiments, the nystagmus testing device may further include a memory that is configured to store data associated with the corresponding test.

In some embodiments, the nystagmus testing device may further include an external display to display the data associated with the corresponding test.

In some embodiments, the nystagmus testing device may further include an indicator button configured to be depressed by the test administrator during the test indicating that one or more signs of intoxication.

BRIEF DESCRIPTION OF THE DRAWINGS

The detailed description particularly refers to the following figures, in which.

DETAILED DESCRIPTION OF THE DRAWINGS

While the concepts of the present disclosure are susceptible to various modifications and alternative forms, specific exemplary embodiments thereof have been shown by way of example in the drawings and will herein be described in detail. It should be understood, however, that there is no intent to limit the concepts of the present disclosure to the particular forms disclosed, but on the contrary, the intention is to cover all modifications, equivalents, and alternatives falling within the spirit and scope of the invention as defined by the appended claims.

Referring now to FIGS. 1-5, a nystagmus testing system 10 for conducting a nystagmus testing routine includes a nystagmus testing device 12 and a telescopic pole 14 connected to the nystagmus testing device 12. The nystagmus testing device 12 further includes a housing 74 that includes a front display 16 facing a test subject and a rear display 40 facing a test administrator such as, for example, a law enforcement officer. The front display 16 is configured to display a subject stimulus 52, while the rear display 40 is configured to display an administrator tracker 54 that is synchronized with the subject stimulus to permit the administrator to independently monitor the subject's eyes.

In use, a test administrator holds the nystagmus testing device 12 between 12 and 15 inches away from a test subject's nose and may adjust the telescopic pole 14 to position the nystagmus testing device 12 slightly above eye level of the test subject to conduct the nystagmus testing routine. During the nystagmus testing routine, a stimulus 52 is displayed on the front display 16, and the test subject is instructed to follow movement of the stimulus 52. Simultaneously, the administrator tracker 54 is displayed on the rear display 40 to reflect the movement of the stimulus 52, such that the test administrator is aware the position of the stimulus 52 when observing the subject's eye movement. In the illustrative embodiment, the nystagmus testing routine includes four nystagmus tests, which are designed for the test administrator to determine lack of smooth pursuit (i.e., a first nystagmus test), distinct and sustained nystagmus at maximum deviation (i.e., a second nystagmus test), onset of nystagmus prior to 45 degrees (i.e., a third nystagmus test), and vertical gaze nystagmus (i.e., a fourth nystagmus test).

Figure 1:
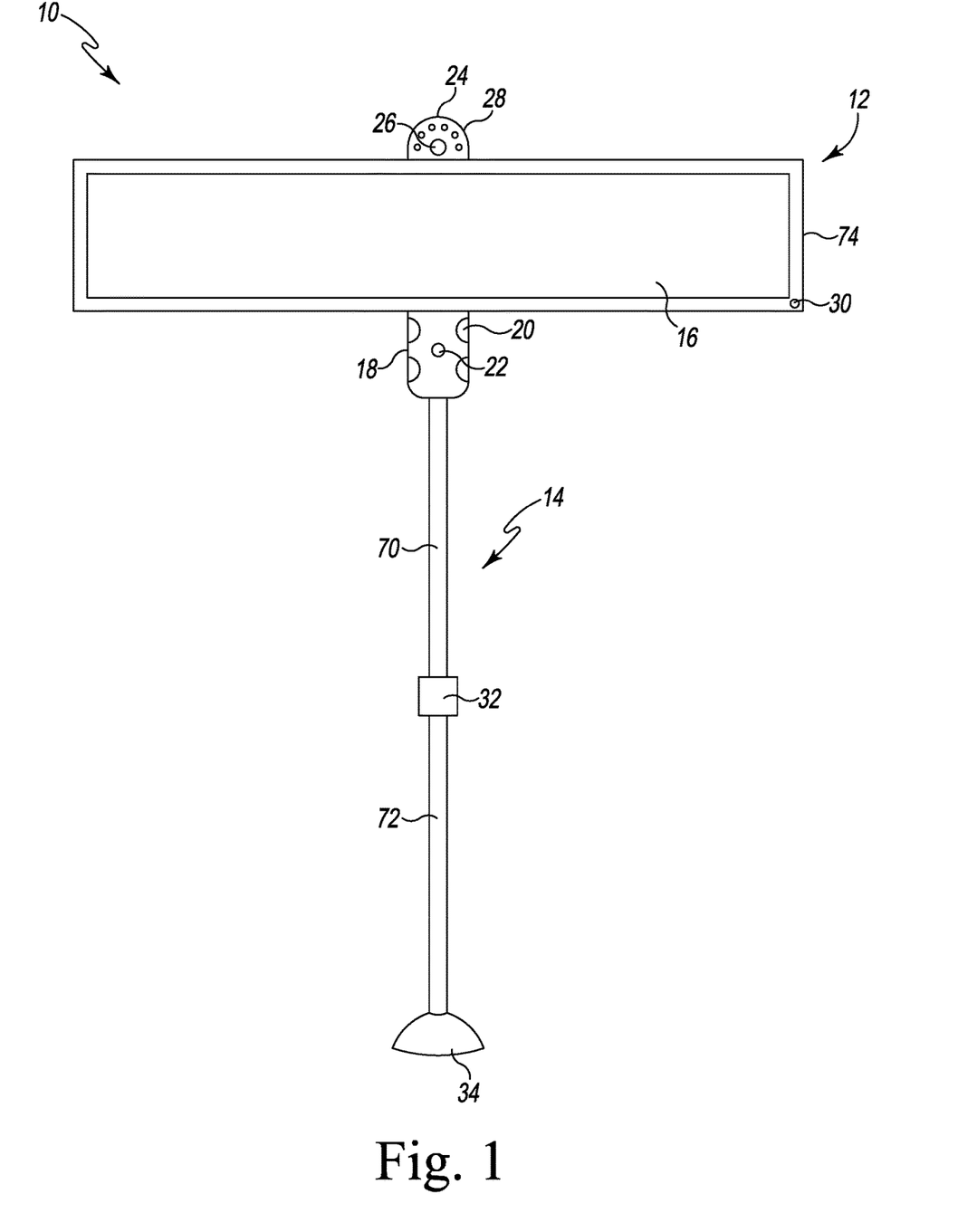
FIG. 1 is a front view of at least one embodiment of a nystagmus testing system including a nystagmus testing device and a telescopic pole.
Figure 3:
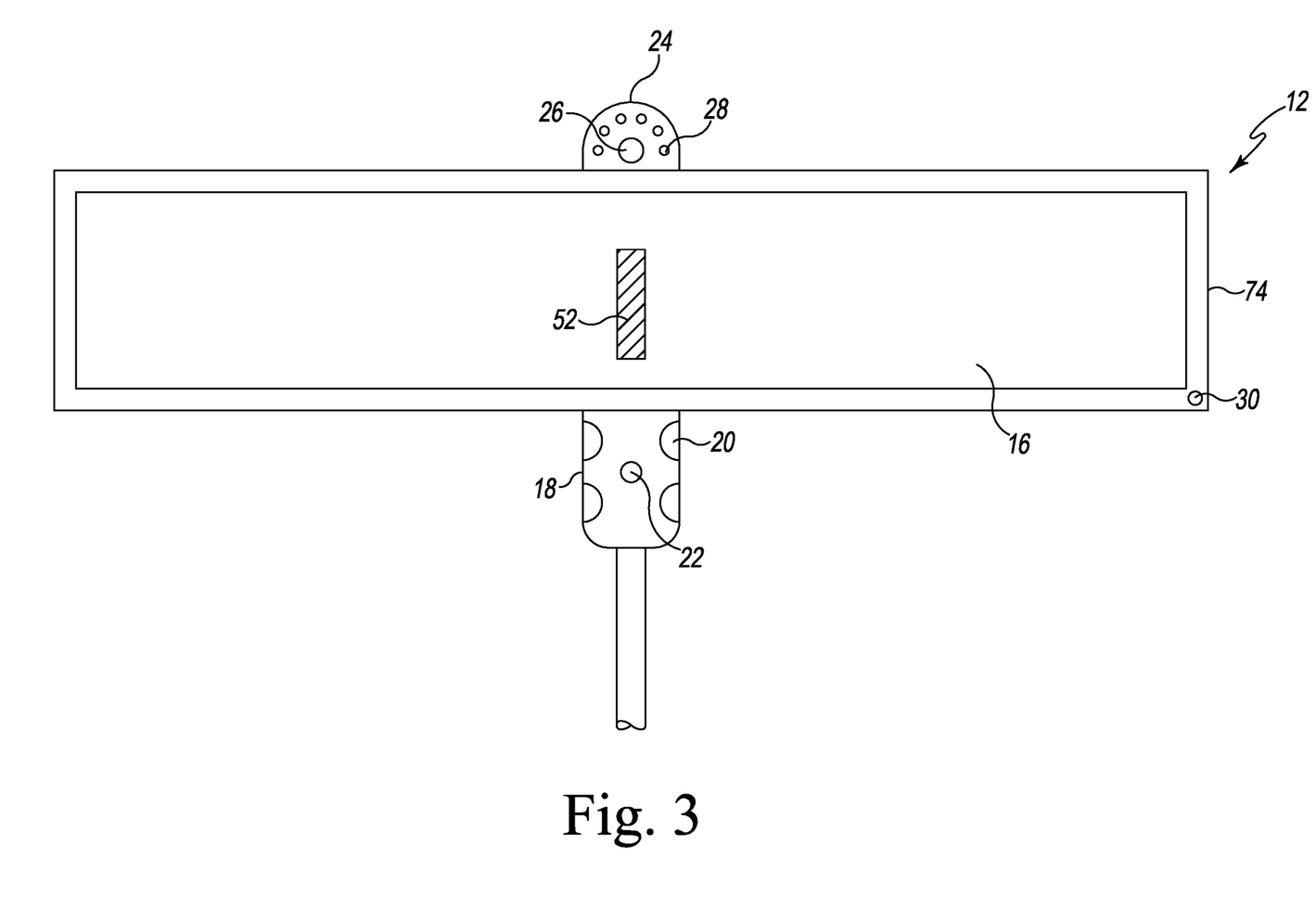
FIG. 3 is a detailed front view of at least one embodiment the nystagmus testing device of the nystagmus testing system of FIGS. 1 and 2.

As shown in FIGS. 1 and 3, the nystagmus testing device 12 includes the housing 74, a head 24 mounted on top of the housing 74, a handle 18 mounted at the bottom of the housing 74, and the telescopic pole 14. A front surface of the housing 74 further includes the front display 16 and a microphone 30 that is configured to receive an audio input. In the illustrative embodiment, the nystagmus testing device 12 is approximately 26 inches in length, approximately 4 inches in width, and approximately 1 to 1.25 inches in height. However, it should be appreciated that, in some embodiments, a dimension of the nystagmus testing device 12 may vary. As discussed above, the nystagmus testing device 12 is connected to the telescopic pole 14. The telescopic pole 14 includes two pole segments 70, 72 that are connected via a locking mechanism 32. The lower pole segment 72 is connected to a base 34 that is configured to provide traction to gripping the surface of the floor. For example, the base 34 may be rectangular, square, oval, or circular.

The head 24 includes a camera 26 and a light source 28 (e.g., a LED or IR). The camera 26 is configured to capture the subject's eye movement during the nystagmus testing routine. The light source 28 is configured to indicate a status of the nystagmus testing routine. For example, the light source 28 on the head 24 may be illuminated in a solid green light indicating that a nystagmus test is currently being conducted, in a moderate flashing pattern indicating that a test restart button 68 has been received, and in solid blue light indicating a successful completion of the nystagmus test.

As discussed above, the front display 16 is configured to display the stimulus 52, as shown in FIG. 3. The movement of the stimulus 52 along the front display 16 depends on a specific nystagmus test of the nystagmus testing routine that is being conducted. During the nystagmus routine, the nystagmus testing system 10 is configured to track the subject's eye movements in relation to the stimulus 52 on the front display 16. To do so, eye-tracking software may be used to follow the eye movements during the nystagmus tests. An exemplary eye-tracking software is TobiiPro, which is commercially available from Tobii Technology, Inc.

For example, during the first nystagmus test, the stimulus 52 is moved from the center position to a test subject's far left and back to the center position twice for each eye at a speed that takes at least two seconds from the center position to the side position. During this time, the test administrator observes whether the subject has or lacks smooth pursuit of the stimulus, and the nystagmus testing system 10 is configured to record the subject's eye movement from the camera 26 and the movement of the stimulus 52.

During the second nystagmus test, the stimulus 52 is moved from the center position to the subject's far left at a rate taking at least two seconds, held for at least four seconds, and then moved back to the center position at the same two-second rate. During this time, the test administrator determines whether the subject has distinct and sustained nystagmus at maximum deviation (i.e., a point at which the eye has moved fully to one side and cannot move any further). Again, the nystagmus testing system 10 is configured to record the subject's eye movement from the camera 26 and the movement of the stimulus 52.

During the third nystagmus test, the stimulus 52 is moved to the side slowly and is held for a predefined time to confirm the onset of nystagmus prior to 45-degrees. In order to estimate a subject's 45-degree angle, the nystagmus testing system 10 determines a point of the subject's 45-degree based on the position of a zero-degree (i.e., when the subject is looking forward) and the position of a maximum deviation at 90-degrees. Using the subject's natural gaze forward and then the subject's gaze at maximum deviation, the nystagmus testing system 10 would determine the point at which the subject's eyes go to 45 degrees. During this time, the test administrator determines whether the onset of nystagmus occurs prior to the eye's movement to a 45-degree deviation. Again, the nystagmus testing system 10 is configured to record the subject's eye movement from the camera 26 and the movement of the stimulus 52.

Lastly, during the fourth nystagmus test, the stimulus 52 is moved up and down. During this time, the test administrator determines whether the person has distinct and sustained nystagmus during vertical gaze, and the nystagmus testing system 10 is configured to record the subject's eye movement from the camera 26 and the movement of the stimulus 52. It should be appreciated that, in some embodiment, the nystagmus testing device 12 may be rotate 90-degree relative to the telescopic pole 14 during the fourth nystagmus test.

Referring back to FIGS. 1 and 3, the handle 18 includes a plurality of pressure sensors 20 and an indicator button 22. The plurality of pressure sensors 20 is configured to determine a stability of the nystagmus testing system 10. In the illustrative embodiment, the handle 18 provides an ergonomic grip for the test administrator to hold the nystagmus testing system 10 during the nystagmus routine. During that time, the nystagmus testing system 10 determines whether the nystagmus testing system 10 was held continuously and stably during each nystagmus test based on input signals received from the plurality of pressure sensors 20. The nystagmus testing system 10 may determine that the nystagmus test has been provided successfully if the nystagmus testing system 10 was held stably for a predefined period of time.

The indicator button 22 is configured to be depressed by the test administrator during the nystagmus tests to record the administrator's note of one or more clues or signs of intoxication. For example, the test administrator may depress the indicator button 22 when an onset of jerking of the subject's eye is observed during the nystagmus tests.

When the indicator button 22 is depressed, a signal is generated and the nystagmus testing system 10 records the time at which the signal was received along with the position of the stimulus 52 and the eye movements of the test subject (e.g., a photo or a video). As discussed below, the test administrator may subsequently add further comments to describe what the test administrator observed (i.e., a present sense impression) at each indicated time.

Figure 2:
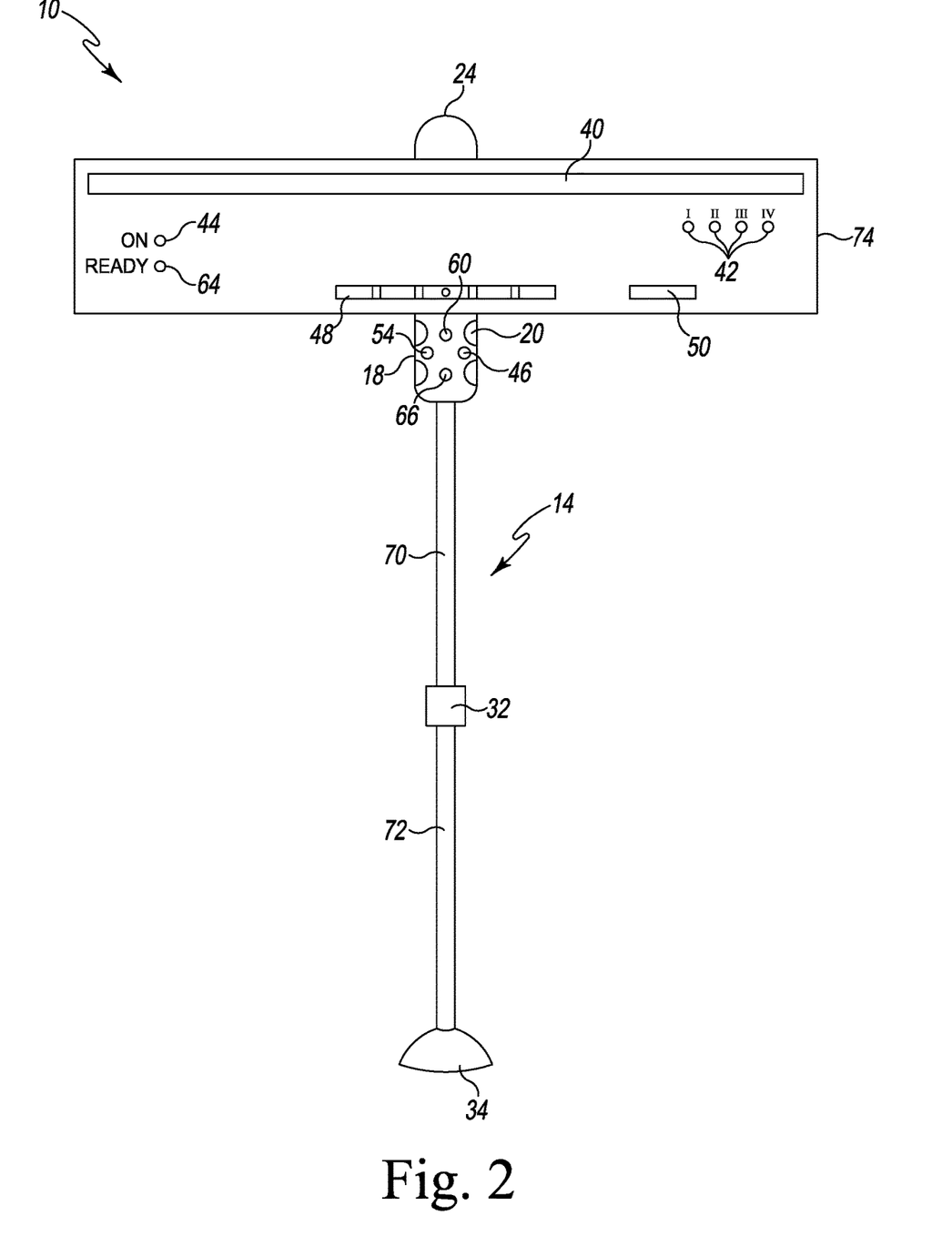
FIG. 2 is a rear view of at least one embodiment of the nystagmus testing system of FIG. 1.
Figure 4:
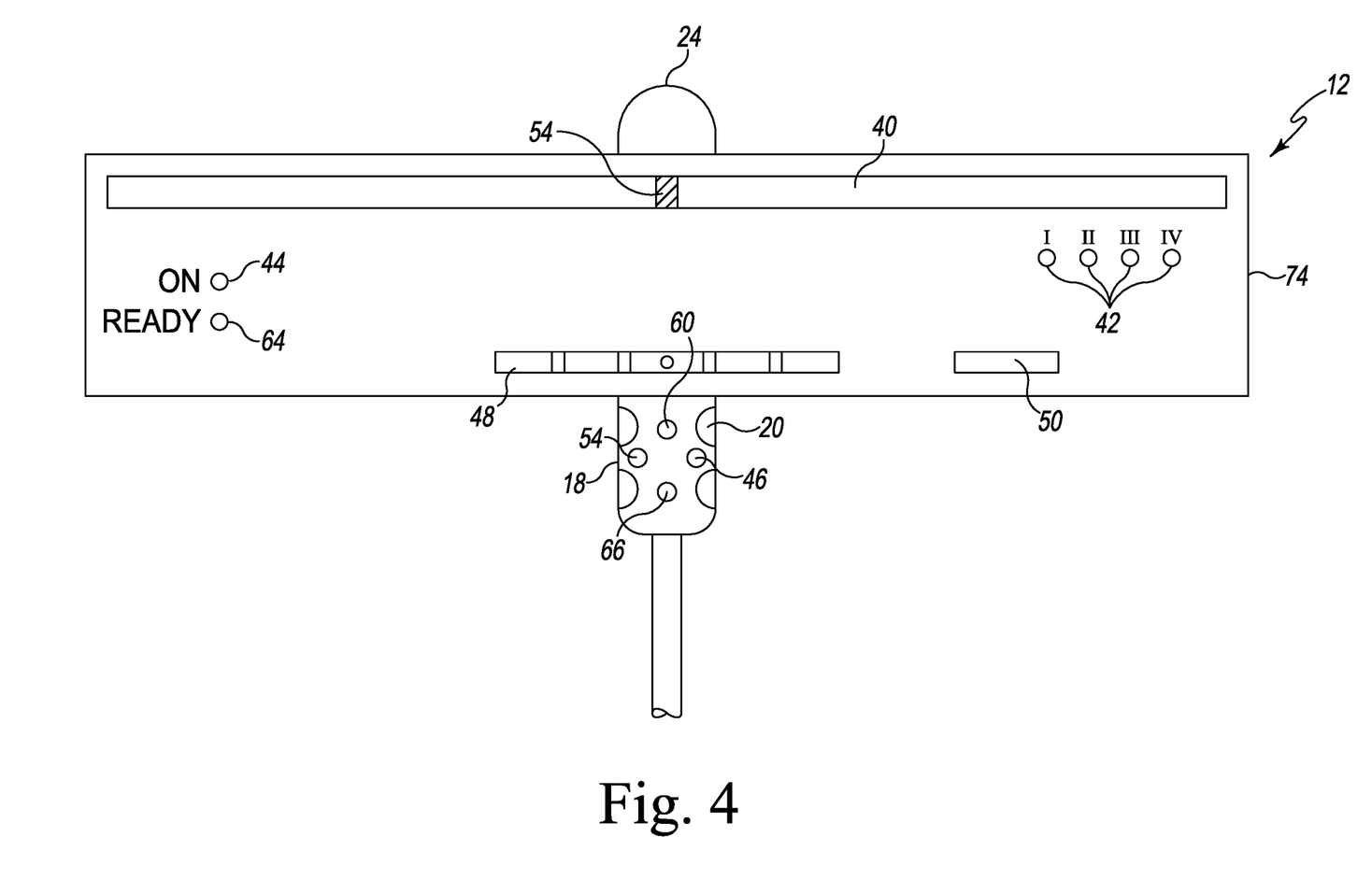
FIG. 4 is a detailed rear view of at least one embodiment the nystagmus testing device of the nystagmus testing system of FIGS. 1 and 2.

Referring now to FIGS. 2 and 4, a rear surface of the housing 74 of the nystagmus testing device 12 further includes the rear display 40, a plurality of test indicators 42, a power indicator 44, a ready indicator 64, a level 48, and an internal shock sensor 50. As discussed above, the rear display 40 is configured to display the administrator tracker 54 that reflects the position of the stimulus 52 displayed on the front display 16. This allows the test administrator to observe the subject's eye movements relative to the position of the administrator tracker 54 to determine whether the subject is correctly following the stimulus 52.

The plurality of test indicators 42 is configured to indicate which nystagmus test of the nystagmus routine is currently being provided. As shown in FIGS. 2 and 4, in the illustrative embodiment, there are four (I, II, III, IV) test indicators 42 (i.e., four nystagmus tests). As discussed above, the first nystagmus test I is associated with a nystagmus test for determining lack of smooth pursuit, and the second nystagmus test II is associated with a nystagmus test for determining distinct and sustained nystagmus at maximum deviation. The third nystagmus test III is associated with a nystagmus test for determining onset of nystagmus prior to 45 degrees, and the fourth nystagmus test IV is associated with a nystagmus test for determining distinct and sustained nystagmus during vertical gaze.

The power indicator 44 is configured to indicate whether the nystagmus testing device 12 is powered on. The ready indicator 64 is configured to indicate whether the nystagmus testing device 12 is ready to perform a nystagmus test. For example, after a successful nystagmus test, the nystagmus testing device 12 may take few seconds to store data related to the successful nystagmus test. Once the nystagmus testing device 12 is ready to perform the next nystagmus test, the ready indicator 64 will be illuminated.

The level 48 is configured to assist the test administrator to hold the nystagmus testing device 12 leveled during the horizontal gaze tests (i.e., the first, second, and third nystagmus tests) and plumbed during the vertical gaze nystagmus test (i.e., the fourth nystagmus test).

Figure 6:
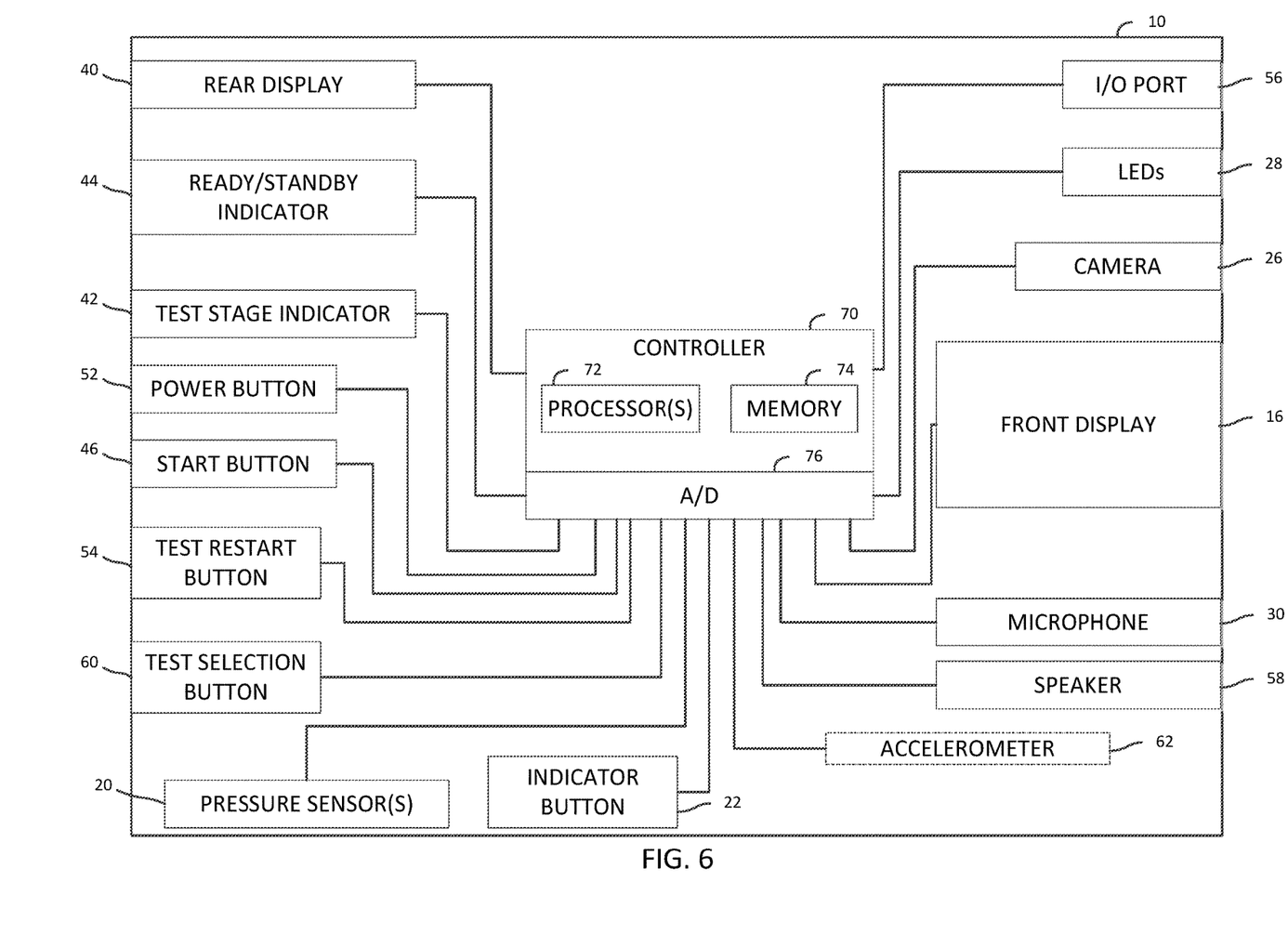
FIG. 6 is a simplified block diagram of components of the nystagmus testing device of FIGS. 1 and 2.

The internal shock sensor 50 is configured to observe sudden movements (e.g., if the nystagmus testing device 12 is dropped or moved abruptly) and outputs a signal for recordation. In some embodiments, the internal shock sensor 50 may be embodied as an accelerometer 62 as shown in FIG. 6.

The handle 18 further includes a start button 46, a power button 66, a test restart button 68, and a test selection button 60. The power button 66 is configured to turn on the nystagmus testing device 12. The start button 46 is configured to generate a start signal to start each nystagmus test of the nystagmus routine. During any nystagmus test, the test administrator may depress the test restart button 68 to generate a restart signal. In response to receiving the restart signal, the nystagmus testing system 10 restarts the corresponding nystagmus test that is currently being provided.

Typically, the nystagmus testing system 10 provides the nystagmus routine in an order from the first nystagmus test to the fourth nystagmus test. However, in the illustrative embodiment, the test administrator may choose to select any nystagmus test during the nystagmus routine. To do so, the test administrator may depress the test selection button 60 until a desired nystagmus test is selected. The test selection button 60 is configured to generate a test selection signal to indicate a nystagmus test selected from the plurality of nystagmus tests. It should be appreciated that, in response to a depression of the test selection button 60, a test indicator 42 associated with the selected nystagmus test will be illuminated.

Figure 5:
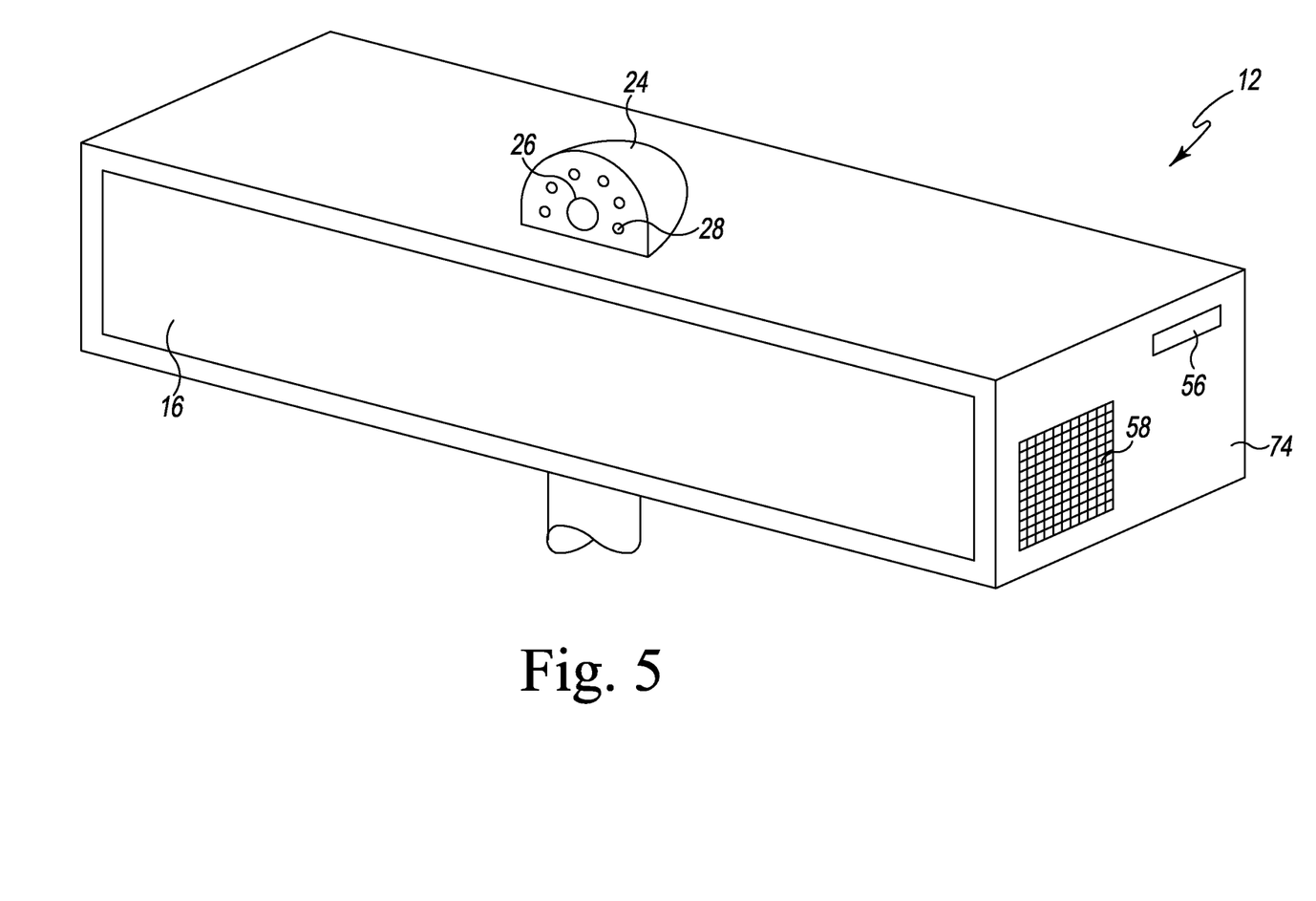
FIG. 5 is a side perspective view of at least one embodiment the nystagmus testing device of the nystagmus testing system of FIGS. 1 and 2.

In the illustrative embodiment, a side surface of the housing 74 of the nystagmus testing device 12 further includes a speaker 58 and a USB connector 56 as shown in FIG. 5. The nystagmus testing device 12 may output instructions for the test subject and/or the test administrator via the speaker 58. The USB connector 56 may be used to transfer nystagmus test data collected by the nystagmus testing device 12. For example, the nystagmus test data may include a list of nystagmus tests that were conducted, a video of the subject's eye movement of each nystagmus test, and the movement of the stimulus 52 of each nystagmus test.

Referring now to FIG. 6, in an illustrative embodiment, the nystagmus testing system 10 includes a controller 80 that is configured to control the operation of the nystagmus testing system 10 to conduct the nystagmus routine. The controller 80 includes one or more processors 82, a memory 84, and an analog-to-digital converter 86. The processor 82 may be embodied as any type of processor capable of performing the functions described herein. For example, the processor 82 may be embodied as a single or multi-core processor(s), digital signal processor, microcontroller, or other processor or processing/controlling circuit.

The memory 84 may be embodied as any type of volatile (e.g., dynamic random access memory (DRAM), etc.) or non-volatile memory or data storage capable of performing the functions described herein. Volatile memory may be a storage medium that requires power to maintain the state of data stored by the medium. Non-limiting examples of volatile memory may include various types of random access memory (RAM), such as dynamic random access memory (DRAM) or static random access memory (SRAM). One particular type of DRAM that may be used in a memory module is synchronous dynamic random access memory (SDRAM). The memory 84 may be configured to store a nystagmus routine including a plurality of nystagmus tests and further store nystagmus data from each of the nystagmus tests, which will be discussed in detail below.

The analog-to-digital converter 86 is configured to receive one or more analog input signal from a plurality of buttons, such as the power button 66, the test start button 46, the test restart button 68, the test selection button 60, one or more pressure sensors 20, and an accelerometer 62 in some embodiment. Additionally, the analog-to-digital converter 86 is configured to receive video contents from the camera 26 facing the subject records the subject's eye movements. The analog-to-digital converter 86 is configured to convert the received input analog signal(s) to an output digital signal(s) for displaying on the front display 16 and the rear display 40. The analog-to-digital converter 76 is also configured to communicate with the microphone 30 and the speaker 58 to receive and/or record an audio and output an instruction(s).

Referring now to FIGS. 7-11, in use, the nystagmus testing system 10 may execute a method 100 to conduct a nystagmus routine. The method 100 begins with block 102 in which the nystagmus testing system 10 is to conduct an initial test to confirm equal tracking and equal pupil size of a test subject prior to starting a nystagmus routine. Subsequently, in block 104 the nystagmus testing system 10 is to receive a start signal from the start button 46 to start a nystagmus routine. In other words, the nystagmus testing system 10 determines whether a test administrator has pressed the start button 46. If the nystagmus testing system 10 determines that the start signal has not been received in block 106, the method 100 loops back to block 104 to continue monitoring and receiving a start signal from the start button 46.

Figure 7:
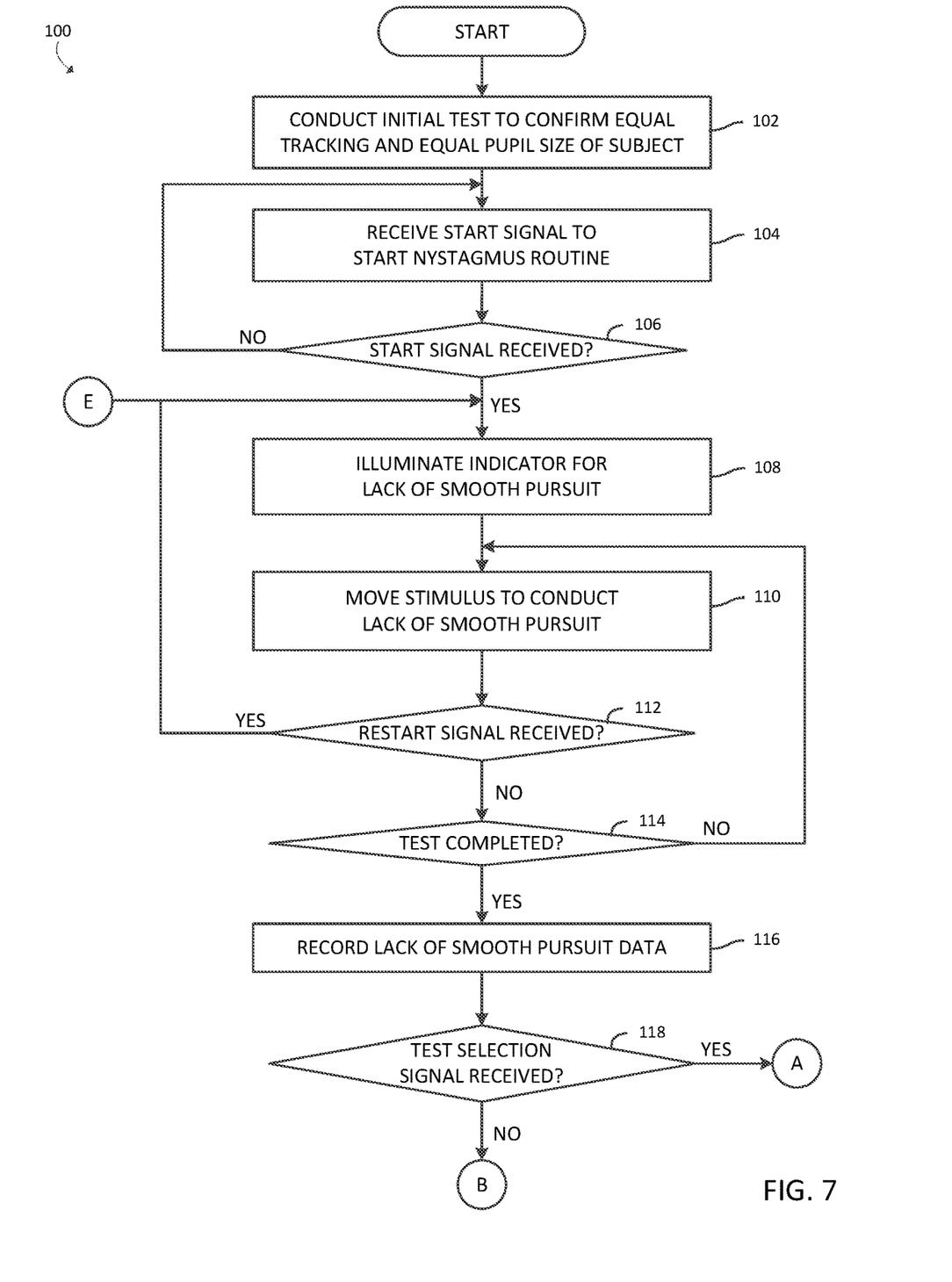
FIGS. 7-11 are simplified flow charts of a nystagmus testing routine of the nystagmus testing device of FIGS. 1 and 2.

If, however, the nystagmus testing system 10 determines that a start signal has been received, the method 100 advances to block 108 to start the nystagmus routine to determine whether a subject exhibits nystagmus. As discussed above, in the illustrative embodiment, the nystagmus routine includes four nystagmus tests, each of which is directed to determining lack of smooth pursuit, distinct and sustained nystagmus at maximum deviation, onset of nystagmus prior to 45 degrees, or vertical gaze nystagmus. In response to receiving a first start signal, the nystagmus testing system 10 starts the first nystagmus test that is directed to determining the lack of smooth pursuit. In doing so, in block 108, the nystagmus testing system 10 illuminates the test indicator 42 to indicate the first nystagmus test that is being conducted and the light source 28 on the head 24 in green color.

Subsequently, in block 110, the nystagmus testing system 10 moves the stimulus 52 on the front display 16 to conduct the first nystagmus test and displays the administrator tracker 54 on the rear display 40 reflecting the position of the stimulus 52. As described above, this allows the test administrator to observe the subject's eye movements relative to the position of the administrator tracker 54 to determine whether the subject is correctly following the stimulus 52. For example, the nystagmus testing system 10 moves the front stimulus from the center position to the subject's far left and back to the center position twice for each eye. During this time, the camera 26 facing the subject records the subject's eye movements, while the test administrator may look for a lack of smooth pursuit by observing the subject's eye movements. If, at any time, the subject lacks smooth pursuit or not following the instruction, the test administrator may restart the test by pressing the restart button 68.

If the restart button 68 is pressed as indicated in block 112, the nystagmus testing system 10 illuminates the light source 28 on the head 24 from a solid green light to a moderate flashing pattern indicating that a restart signal has been received, and the method 100 loops back to block 108 to restart the first nystagmus test. If, however, the restart signal is not received, the method 100 advances to block 114 to determine whether the first nystagmus test has been completed. If the nystagmus testing system 10 determines that the first nystagmus test has not been completed, the method 100 loops back to block 110 to continue moving the stimulus 52 to conduct the first nystagmus test. If, however, the nystagmus testing system 10 determines that the first nystagmus test is completed in block 114, the method 100 advances to block 116 in which the nystagmus testing system 10 records the first nystagmus test data. The nystagmus test data includes the movement of the stimulus 52, a video content captured by the camera 26 of the subject's eye movements relative to the position of the stimulus 52, and all of the buttons depressed on the nystagmus testing system 10 during the first nystagmus test.

Subsequently, the nystagmus testing system 10 determines whether a test selection signal is received in block 118. If so, the method 100 skips ahead to block 162 of FIG. 11 to determine a selected nystagmus test indicated by the test selection signal, which will be discussed in detail below. If, however, the nystagmus testing system 10 determines that the test selection signal has not been received, the method 100 advances to block 120 of FIG. 8.

Figure 8:
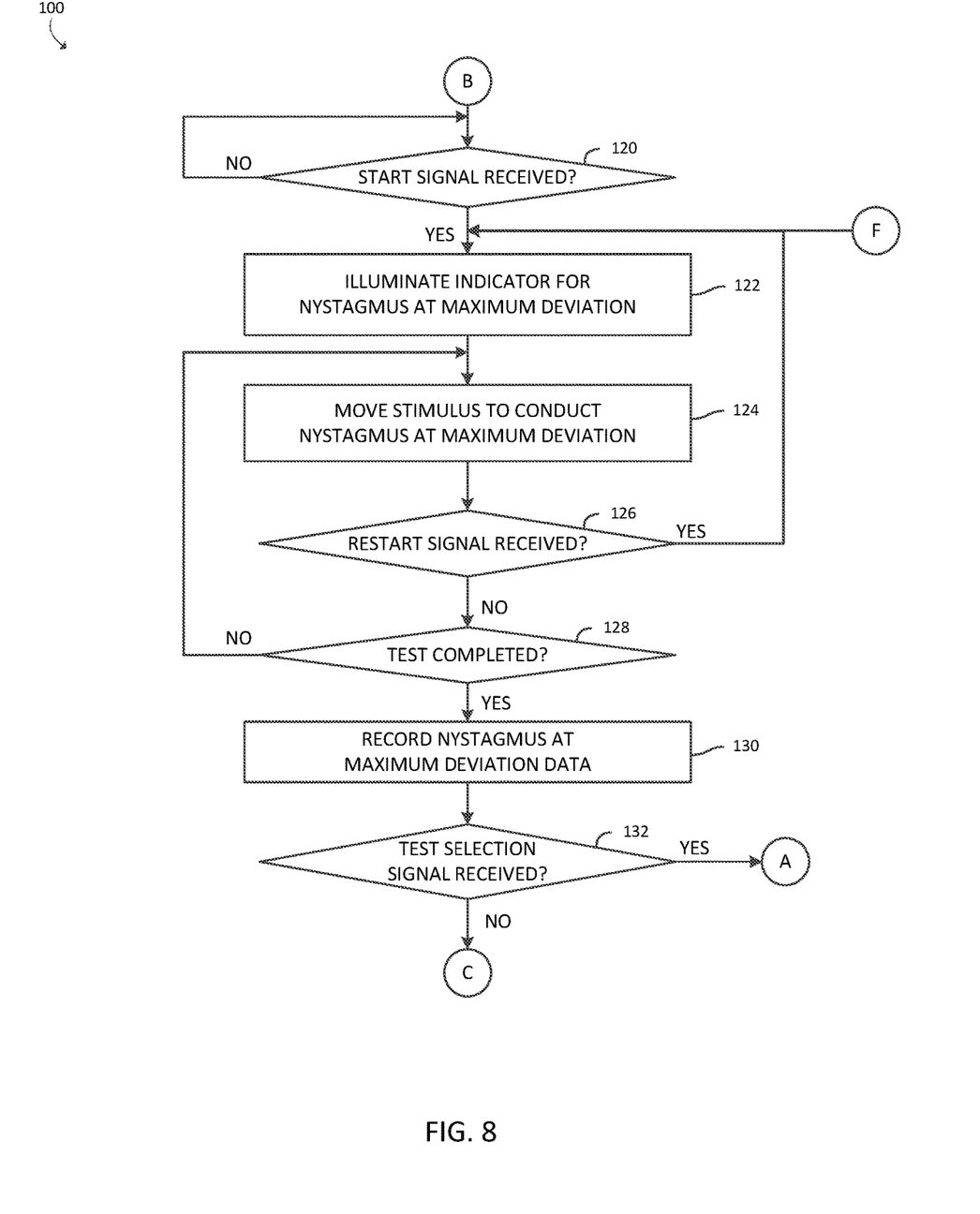

In block 120, the nystagmus testing system 10 determines whether another start signal has been received. If the nystagmus testing system 10 determines that a start signal has not been received, the method 100 loops back to block 120 to continue monitoring for a start signal. If, however, the nystagmus testing system 10 determines that a start signal has been received, the method 100 advances to block 122 to start the second nystagmus test, which is directed to determining distinct and sustained nystagmus at maximum deviation.

In block 122, the nystagmus testing system 10 illuminates the test indicator 42 to indicate the second nystagmus test that is being conducted and the light source 28 on the head 24 in green color. Subsequently, the nystagmus testing system 10 moves the stimulus 52 on the front display 16 to conduct the second nystagmus test in block 124. As discussed above, the nystagmus testing system 10 also displays the administrator tracker 54 on the rear display 40 to reflect the position at which the stimulus 52 is displayed on the front display 16. During this time, the test administrator observes whether the test subject's eyes exhibit nystagmus at maximum deviation. Additionally, the nystagmus testing system 10 determines whether a restart signal has been received.

If the restart button 68 is pressed as indicated in block 126, the nystagmus testing system 10 illuminates the light source 28 on the head 24 from a solid green light to a moderate flashing pattern indicating that a restart signal has been received, and the method 100 loops back to block 122 to restart the second nystagmus test. If, however, the restart signal is not received, the method 100 advances to block 128 to determine whether the second nystagmus test has been completed. If the nystagmus testing system 10 determines that the second nystagmus test has not been completed, the method 100 loops back to block 124 to continue moving the stimulus 52 to conduct the second nystagmus test. If, however, the nystagmus testing system 10 determines that the second nystagmus test is completed in block 128, the method 100 advances to block 130 in which the nystagmus testing system 10 records second nystagmus test data. The second nystagmus test data includes the movement of the stimulus 52, a video content captured by the camera 26 of the subject's eye movements relative to the position of the stimulus 52, and all of the buttons depressed on the nystagmus testing system 10 during the second nystagmus test.

Subsequently, the nystagmus testing system 10 determines whether a test selection signal is received in block 132. If so, the method 100 skips ahead to block 162 of FIG. 11 to determine a selected nystagmus test indicated by the test selection signal, which will be discussed in detail below. If, however, the nystagmus testing system 10 determines that the test selection signal has not been received, the method 100 advances to block 134 of FIG. 9.

Figure 9:
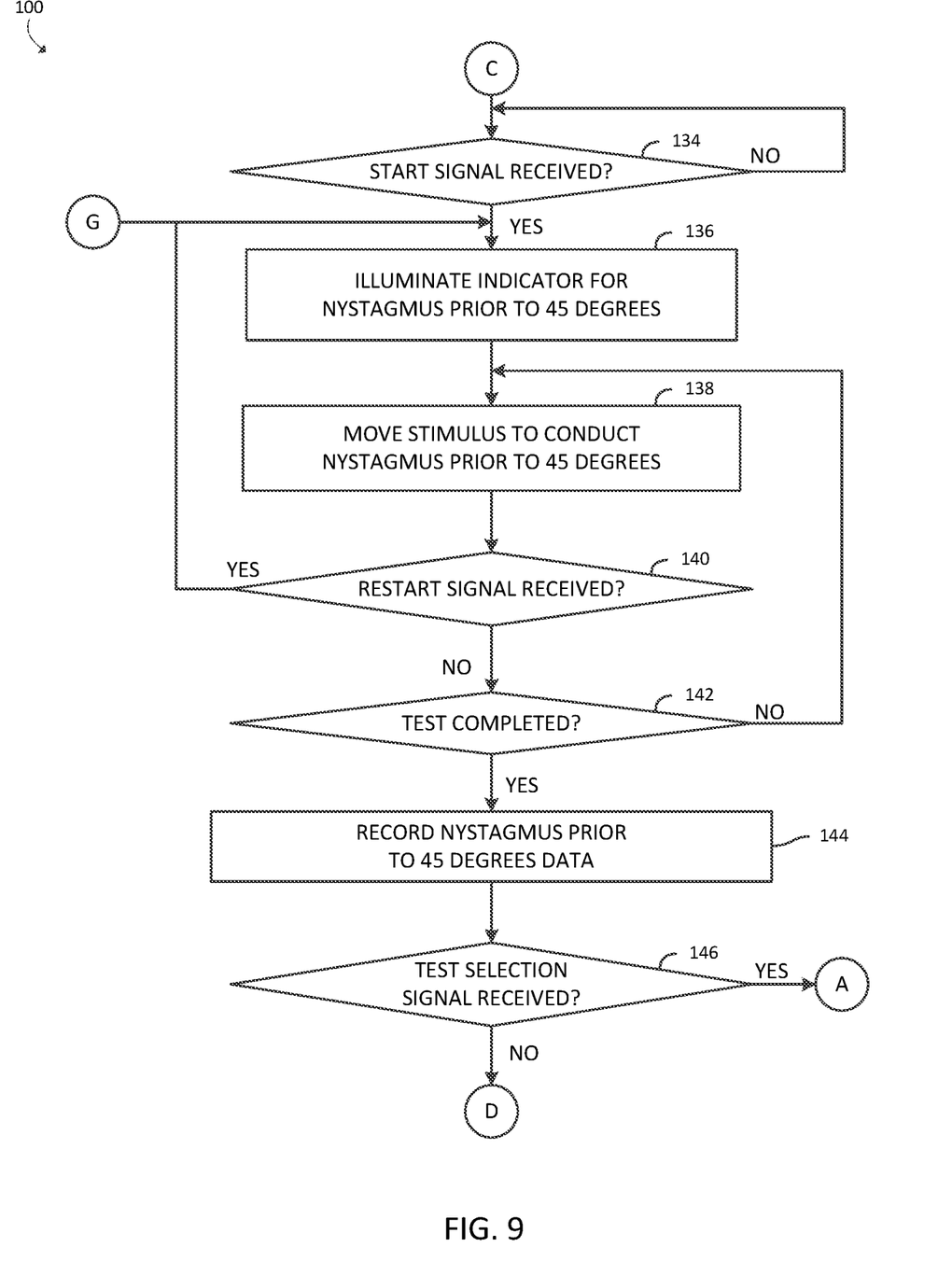

In block 134, the nystagmus testing system 10 determines whether another start signal has been received. If the nystagmus testing system 10 determines that a start signal has not been received, the method 100 loops back to block 134 to continue monitoring for a start signal. If, however, the nystagmus testing system 10 determines that a start signal has been received, the method 100 advances to block 136 to start the third nystagmus test, which is directed to determining onset of nystagmus prior to 45 degrees.

In block 136, the nystagmus testing system 10 illuminates the test indicator 42 to indicate the third nystagmus test that is being conducted and the light source 28 on the head 24 in green color. Subsequently, the nystagmus testing system 10 moves the stimulus 52 on the front display 16 to conduct the third nystagmus test in block 138. As discussed above, the nystagmus testing system 10 also displays the administrator tracker 54 on the rear display 40 to reflect the position at which the stimulus 52 is displayed on the front display 16. During this time, the test administrator observes whether the test subject's eyes exhibit onset of nystagmus prior to 45 degrees. Additionally, the nystagmus testing system 10 determines whether a restart signal has been received in block 140.

If the restart button 68 is pressed as indicated in block 126, the nystagmus testing system 10 illuminates the light source 28 on the head 24 from a solid green light to a moderate flashing pattern indicating that a restart signal has been received, and the method 100 loops back to block 136 to restart the third nystagmus test. If, however, the restart signal is not received, the method 100 advances to block 142 to determine whether the third nystagmus test has been completed. If the nystagmus testing system 10 determines that the third nystagmus test has not been completed, the method 100 loops back to block 138 to continue moving the stimulus 52 to conduct the third nystagmus test. If, however, the nystagmus testing system 10 determines that the third nystagmus test is completed in block 142, the method 100 advances to block 144 in which the nystagmus testing system 10 records third nystagmus test data. The third nystagmus test data includes the movement of the stimulus 52, a video content captured by the camera 26 of the subject's eye movements relative to the position of the stimulus 52, and all of the buttons depressed on the nystagmus testing system 10 during the third nystagmus test.

Subsequently, the nystagmus testing system 10 determines whether a test selection signal is received in block 146. If so, the method 100 skips ahead to block 162 of FIG. 11 to determine a selected nystagmus test indicated by the test selection signal, which will be discussed in detail below. If, however, the nystagmus testing system 10 determines that the test selection signal has not been received, the method 100 advances to block 148 of FIG. 10.

Figure 10:
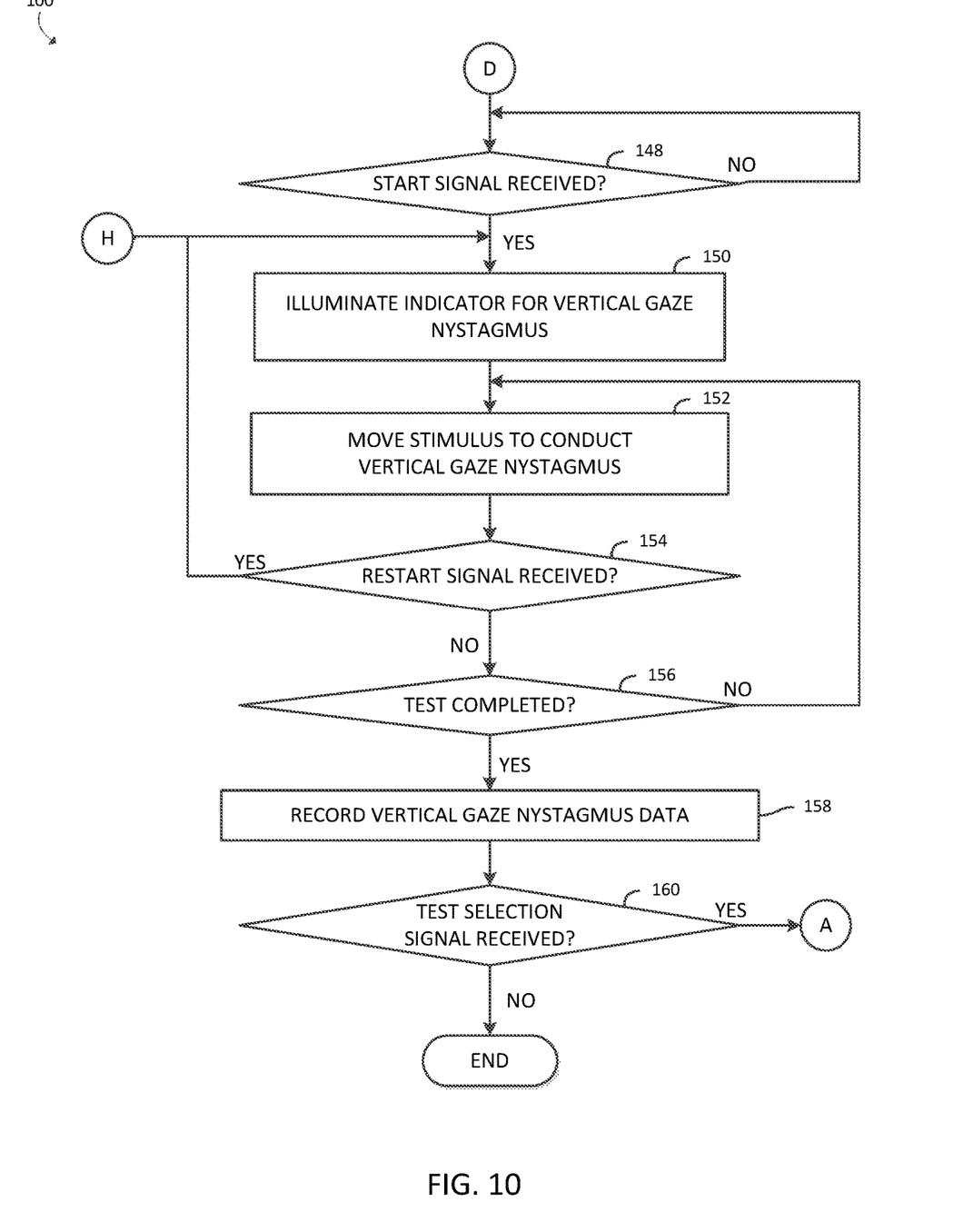
Figure 11:
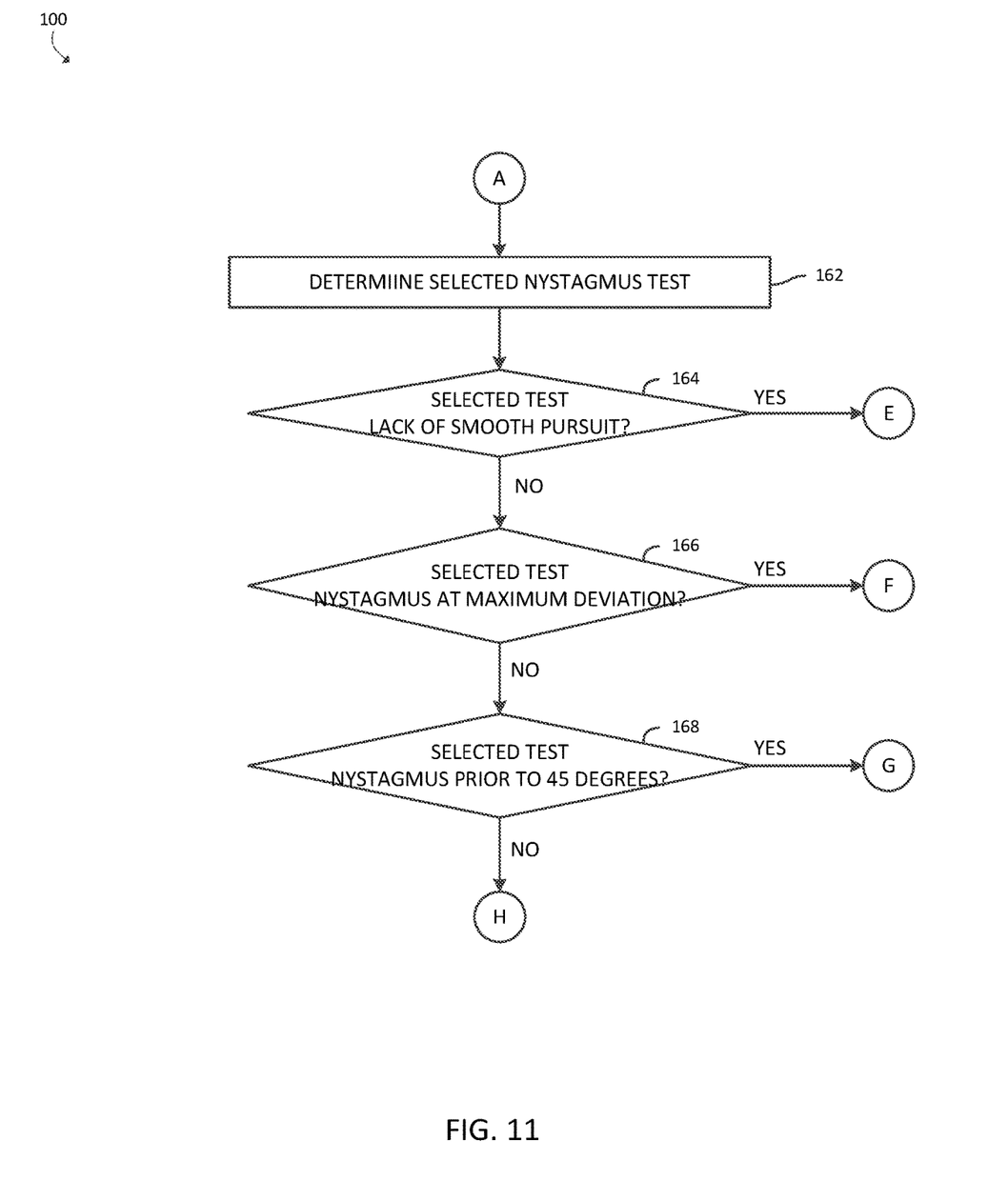

In block 148, the nystagmus testing system 10 determines whether another start signal has been received. If the nystagmus testing system 10 determines that a start signal has not been received, the method 100 loops back to block 148 to continue monitoring for a start signal. If, however, the nystagmus testing system 10 determines that a start signal has been received, the method 100 advances to block 150 to start the fourth nystagmus test, which is directed to determining vertical gaze nystagmus.

In block 122, the nystagmus testing system 10 illuminates the test indicator 42 to indicate the fourth nystagmus test that is being conducted and the light source 28 on the head 24 in green color. Subsequently, the nystagmus testing system 10 moves the stimulus 52 on the front display 16 to conduct the fourth nystagmus test in block 152. As discussed above, the nystagmus testing system 10 also displays the administrator tracker 54 on the rear display 40 to indicate the position at which the stimulus 52 is present in the front display 16. During this time, the test administrator observes whether the test subject's eyes exhibit vertical gaze nystagmus. Additionally, the nystagmus testing system 10 determines whether a restart signal has been received.

If the restart button 68 is pressed as indicated in block 154, the nystagmus testing system 10 illuminates the light source 28 on the head 24 from a solid green light to a moderate flashing pattern indicating that a restart signal has been received, and the method 100 loops back to block 150 to restart the fourth nystagmus test. If, however, the restart signal is not received, the method 100 advances to block 156 to determine whether the fourth nystagmus test has been completed. If the nystagmus testing system 10 determines that the fourth nystagmus test has not been completed, the method 100 loops back to block 152 to continue moving the stimulus 52 to conduct the fourth nystagmus test. If, however, the nystagmus testing system 10 determines that the fourth nystagmus test is completed in block 156, the method 100 advances to block 158 in which the nystagmus testing system 10 records fourth nystagmus test data. The fourth nystagmus test data includes the movement of the stimulus 52, a video content captured by the camera 26 of the subject's eye movements relative to the position of the stimulus 52, and all of the buttons depressed on the nystagmus testing system 10 during the fourth nystagmus test.

Subsequently, the nystagmus testing system 10 determines whether a test selection signal is received in block 160. If not, the nystagmus testing system 10 ends the nystagmus routine. If, however, the nystagmus testing system 10 determines that a test selection signal has been received, the method 100 skips ahead to block 162 of FIG. 11 to determine a selected nystagmus test indicated by the test selection signal.

Subsequently, the nystagmus testing system 10 determines whether the test selection signal indicates that the selected nystagmus test is for determining lack of smooth pursuit (i.e., the first nystagmus test), distinct and sustained nystagmus at maximum deviation (i.e., the second nystagmus test), onset of nystagmus prior to 45 degrees (i.e., the third nystagmus test), or vertical gaze nystagmus (i.e., the fourth nystagmus test). If the nystagmus testing system 10 determines that the selected nystagmus test is the first nystagmus test in block 164, the method 100 loops back to block 108 of FIG. 7 to start the first nystagmus test. If not, the nystagmus testing system 10 determine whether the selected nystagmus test is the second nystagmus test in block 166. If so, the method 100 loops back to block 122 of FIG. 8 to start the second nystagmus test. If not, the method 100 advances to block 168 to determine whether the selected nystagmus test is the third nystagmus test. If so, the method 100 loops back to block 136 of FIG. 9 to start the third nystagmus test. If not, the method 100 advances to block 150 of FIG. 10 to start the fourth nystagmus test.

Figure 12:
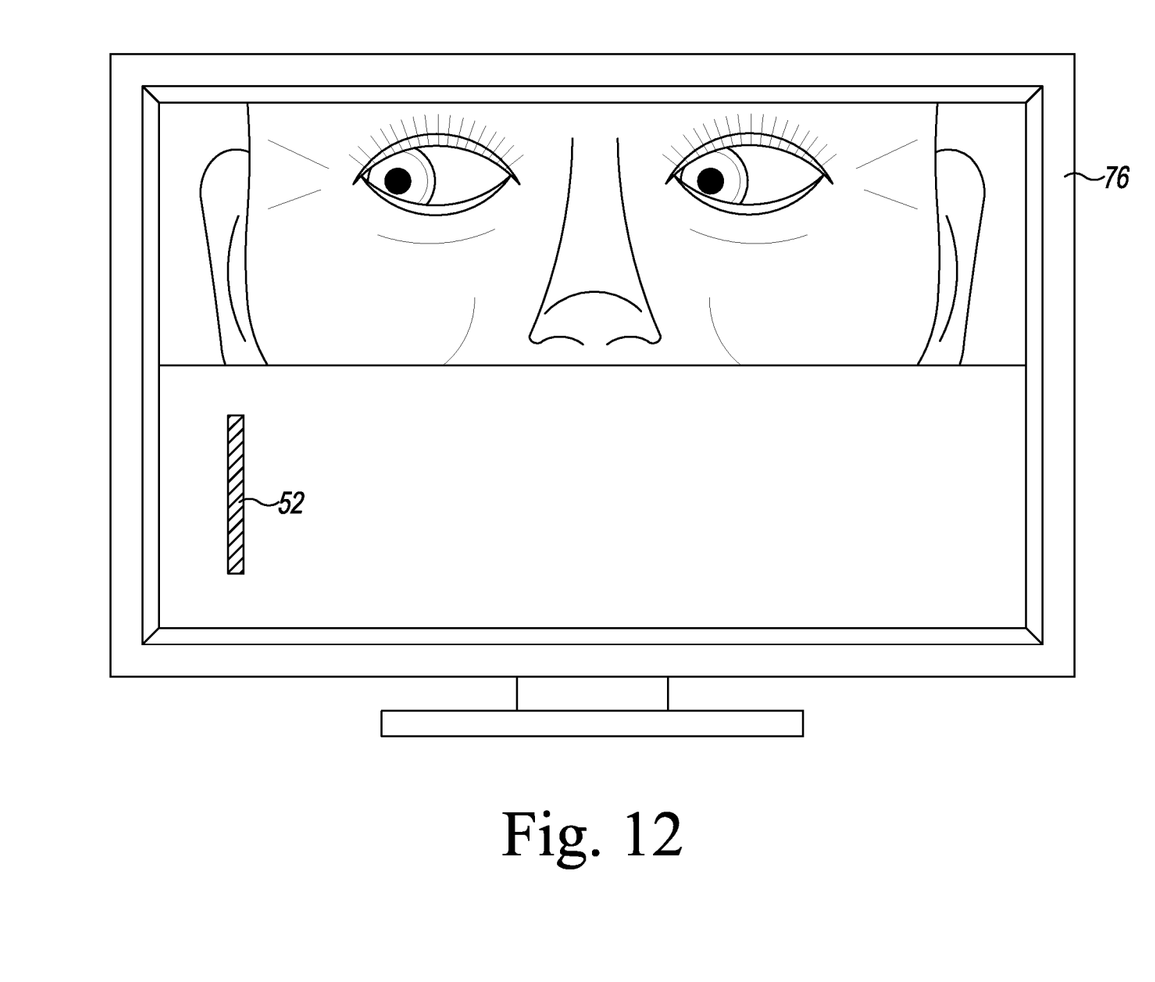
FIG. 12 is a front view of at least one embodiment of an external display displaying nystagmus data obtained during the nystagmus testing routine.

Referring now to FIG. 12, the nystagmus testing system 10 may include an external display 76 that is configured to display nystagmus test data obtained during the nystagmus testing routine. In the illustrative embodiment, after the nystagmus testing routine is completed, the test administrator may transfer the nystagmus test data of the nystagmus testing routine to a computing device via a USB cable. However, it should be appreciated that, in some embodiments, the nystagmus testing device 12 may be communicatively coupled to the computing device to transfer the nystagmus test data. In such embodiments, the nystagmus testing device 12 may be configured to use any one or more communication technologies (e.g., wireless or wired communications) and associated protocols (e.g., Ethernet, Bluetooth®, Wi-Fi®, WiMAX, LTE, 4G, 5G, etc.) to effect such communication.

In some embodiments, the computing device may display the nystagmus test data on the external display 76. In the illustrative embodiment, the nystagmus test data is generated for each nystagmus test and may include the movement of the stimulus 52, a video content captured by the camera 26 of the subject's eye movements relative to the position of the stimulus 52, all of the buttons depressed on the nystagmus testing system 10, and one or more indicators or flags that indicate the time at which the test administrator observed one or more signs (e.g., jerking of the subject's eye) of intoxication. The test administrator may review the nystagmus test data to verify the test administrator's observation prior to concluding the sobriety of the test subject. For example, as shown in FIG. 12, the external display 76 displays a subject's eye movement captured by the camera 26 on a top half of the external display 76 and the position of the subject stimulus 52 on a bottom half of the external display 76. The external display 76 may further display an indicator or flag to indicate the time at which the test administrator observed one or more signs of intoxication. While reviewing the nystagmus test data, the test administrator may add notes or comments regarding the test administrator's observations.

Additionally, the computing device may further upload the nystagmus test data to a database for storage. For example, such nystagmus test data may be retrieved from another computing device to replay the nystagmus test data to verify the test administrator's observation and that the nystagmus test was administered correctly.

While the disclosure has been illustrated and described in detail in the drawings and foregoing description, such an illustration and description is to be considered as exemplary and not restrictive in character, it being understood that only illustrative embodiments have been shown and described and that all changes and modifications that come within the spirit of the disclosure are desired to be protected. It should be appreciated that the order of the nystagmus tests may vary depending on how the nystagmus routine was initialized or programed.

There are a plurality of advantages of the present disclosure arising from the various features of the method, apparatus, and system described herein. It will be noted that alternative embodiments of the method, apparatus, and system of the present disclosure may not include all of the features described yet still benefit from at least some of the advantages of such features. Those of ordinary skill in the art may readily devise their own implementations of the method, apparatus, and system that incorporate one or more of the features of the present invention and fall within the spirit and scope of the present disclosure as defined by the appended claims.

The invention claimed is:

1. A nystagmus testing device comprising:
a camera positioned in a housing and configured to face a test subject to capture eye movements of the test subject,
a start button configured to start a nystagmus routine, the nystagmus routine including a plurality of tests,
a front display positioned in the housing and configured to face the test subject to display a visual stimulus,
a rear display positioned in the housing and configured to face a test administrator to display a visual tracker, and
a controller configured to (i) control movements of the visual stimulus and the visual tracker on the front and rear displays, respectively, such that a position of the visual tracker on the rear display reflects a position of the visual stimulus on the front display, allowing the test administrator to directly observe test subject's eye movements relative to the position of the visual tracker to determine whether the test subject is correctly following the visual stimulus, and
(ii) generate data related to the nystagmus routine and the test subject.

2. The nystagmus testing device of claim 1, wherein each of the plurality of tests is directed to determining one of lack of smooth pursuit, distinct and sustained nystagmus at maximum deviation, onset of nystagmus prior to 45 degrees, and vertical gaze nystagmus.

3. The nystagmus testing device of claim 1, further comprising an indicator indicative of a corresponding test of the nystagmus routine, wherein the indicator is one of a visual indicator and an audible indicator.

4. The nystagmus testing device of claim 3, wherein the visual indicator is configured to illuminate a first color indicating that the corresponding test is ready or completed and a second color indicating that the corresponding test is started.

5. The nystagmus testing device of claim 3, wherein the indicator is configured to indicate which of the plurality of tests is currently being performed.

6. The nystagmus testing device of claim 3, wherein the indicator is configured to indicate, before the start of the nystagmus routine, which of the plurality of tests will be performed.

7. The nystagmus testing device of claim 1, further comprising a test restart button to restart the corresponding test.

8. The nystagmus testing device of claim 1, further comprising a test selection button configured to select one test of the nystagmus routine.

9. The nystagmus testing device of claim 1, further comprising a plurality of pressure sensors configured to determine a stability of the nystagmus testing device.

10. The nystagmus testing device of claim 1, further comprising a LED light configured to illuminate a first color indicating that the corresponding test is ready or completed and a second color indicating that the corresponding test has started.

11. The nystagmus testing device of claim 1, wherein the controller further includes a memory that is configured to store data associated with the corresponding test.

12. The nystagmus testing device of claim 11, further comprising an external display to display the data associated with the corresponding test.

13. The nystagmus testing device of claim 1, wherein the data includes eye movements of the test subject and positions of the visual stimulus during the corresponding test.

14. The nystagmus testing device of claim 1, wherein the controller is configured to perform the nystagmus routine without requiring the test administer to monitor the eye movements of the test subject.

15. The nystagmus testing device of claim 1, wherein the controller is configured to perform the nystagmus routine without the test administer moving a visual stimulus.

* * * * *